United States Patent [19]

Puckette

[11] 4,277,978
[45] Jul. 14, 1981

[54] ADAPTIVE INPUT CIRCUIT

[75] Inventor: Charles M. Puckette, Scotia, N.Y.

[73] Assignee: General Electric Company, Schenectady, N.Y.

[21] Appl. No.: 112,852

[22] Filed: Jan. 17, 1980

[51] Int. Cl.³ ............................................. G01N 29/00
[52] U.S. Cl. ..................................... 73/632; 73/625; 330/284
[58] Field of Search ................ 73/620, 625, 626, 628, 73/629, 632, 641; 330/284; 333/172, 173; 310/319, 334, 336; 367/135; 128/660

[56] References Cited

U.S. PATENT DOCUMENTS

| 3,185,936 | 5/1965 | Fuller | 330/135 |
|---|---|---|---|
| 3,701,059 | 10/1972 | Nyswander | 333/173 |
| 3,967,209 | 6/1976 | Skoures | 330/86 |
| 4,048,573 | 9/1977 | Evans et al. | 330/284 |
| 4,234,940 | 11/1980 | Iinuma | 73/626 |

Primary Examiner—Stephen A. Kreitman
Attorney, Agent, or Firm—Donald R. Campbell; James C. Davis; Marvin Snyder

[57] ABSTRACT

An input circuit is disclosed for variably adapting the dynamic range of an ultrasonic frequency electrical signal to the dynamic range of a signal receiver to which the signal is applied. A band pass filter admits the appropriate band of signal frequencies to the receiver to provide optimum signal-to-noise conditions. A JFET device is shunted across the receiver input and its drain-to-source impedance is varied to control the peak voltage developed by the signal. Control of the impedance of the JFET device may be effected in a pre-programmed manner as a function of time, in response to the amplitude of the signal applied to the receiver input, or in response to both. In either case, the amplitude of the applied signal is constrained to remain substantially within the dynamic range of the receiver.

18 Claims, 3 Drawing Figures

ADAPTIVE INPUT CIRCUIT

The present invention relates in general to new and improved adaptive circuits, in particular to a circuit which adapts the dynamic range of a signal applied to a signal receiver to the dynamic range of the receiver itself.

Receivers having a large dynamic signal range are known in the art. Typically, the receiver is built as a discrete amplifier in which the parameters of each component are specifically selected to obtain the desired performance. When the system uses a number of parallel signal channels, e.g., in an array based system, a separate amplifier is required for each channel. For this type of system, significant economies may therefore be effected by the use of commercially available monolithic integrated amplifiers, such as the MC1733 video amplifier commercially available from Motorola Semiconductor Company, rather than a discrete component amplifier.

When the integrated circuit amplifier is used to implement a multichannel receiver, the amplifier parameters such as dynamic range and sensitivity are fixed. As such, they may fail to meet the requirements of the system in which the gain block is to be used. For example, the dynamic range of a particular receiver may be too limited to handle the dynamic range of the applied signal. For purposes of the present discussion, the dynamic range of the receiver of a specified signal channel is determined, on the high end, by the level of the input signal that causes clipping of the output signal to occur. On the low end, the dynamic range of the receiver is determined by the minimum discernable signal (MDS), the latter being the smallest signal that can be received without being masked by the internal noise of the receiver. The internal noise of the receiver is typically reflected to the receiver input and it may be modeled as a series rms noise voltage, $e_N$, and a shunt rms noise current, $i_N$. This represents an internal noise resistance $R_N$ which must equal the source resistance seen by the receiver of the particular signal channel in order to obtain maximum sensitivity.

Where an ultrasonic transducer array is used with a monolithic multi-channel video amplifier unit, each piezoelectric transducer of the array forms an ultrasonic signal source for one channel of the aforesaid multichannel unit. Each such transducer may be modeled as a current source for its correspnding receiver. Since monolithic units of the type mentioned above require a voltage input signal, a current-to-voltage conversion must be performed in each signal channel. This may be inexpensively accomplished by connecting a resistor in parallel with the aforesaid transducer of the array, the value of said resistor being equal to $R_N$ so as to maximize sensitivity. At a particular current level, the resistance $R_N$ times the current will produce a voltage that causes clipping in the receiver. Thus, the ratio of the MDS current to the maximum current at which clipping will occur defines the dynamic range of the receiver.

For a unit of the type under consideration, the dynamic range of the respective receiver channels is typically 60–70 dB, depending on the bandwidth and the details of the overall receiver amplifier design. The signals provided by the respective piezoelectric transducers of the transducer array typically have a dynamic range on the order of 90 dB. Thus, in order to take advantage of the economies that flow from the use of a commercially available monolithic, video amplifier unit, it is necessary to adapt the dynamic range of the signal derived from each piezoelectric transducer to the dynamic range of the receiver in the corresponding signal channel. This must be done within the constraints imposed by the requirement for matching the receiver to the source in order to maximize sensitivity. The present invention provides a circuit for use in the respective signal channels of such an arrangement which accomplishes these ends.

OBJECTS OF THE INVENTION

It is an object of the present invention to provide a circuit for adapting the dynamic range of an electrical signal derived from an ultrasonic signal source to the dynamic range of a signal receiver.

It is another object of the present invention to provide a circuit for variably compressing the dynamic range of an ultrasonic electrical signal when the signal dynamic range exceeds a limit determined by the dynamic range of the receiver to which the signal is applied.

It is a further object of the present invention to provide a circuit for variably adapting the dynamic range of an ultrasonic signal to the dynamic range of a signal receiver within a frequency pass band selected to achieve signal-to-noise optimization of the receiver.

It is still another object of the present invention to provide a circuit for conforming the dynamic range of a signal derived from one of a plurality of piezoelectric transducers to the dynamic range of a corresponding amplifier in a multi-channel receiver unit, where such circuit may be readily and economically adapted to operate in each signal channel at the center frequency of the corresponding transducer.

These and other objects of the present invention, together with the features and advantages thereof, will become apparent from the following detailed specification when considered jointly with the accompanying drawings.

DESCRIPTION OF INVENTION

Figure 1:
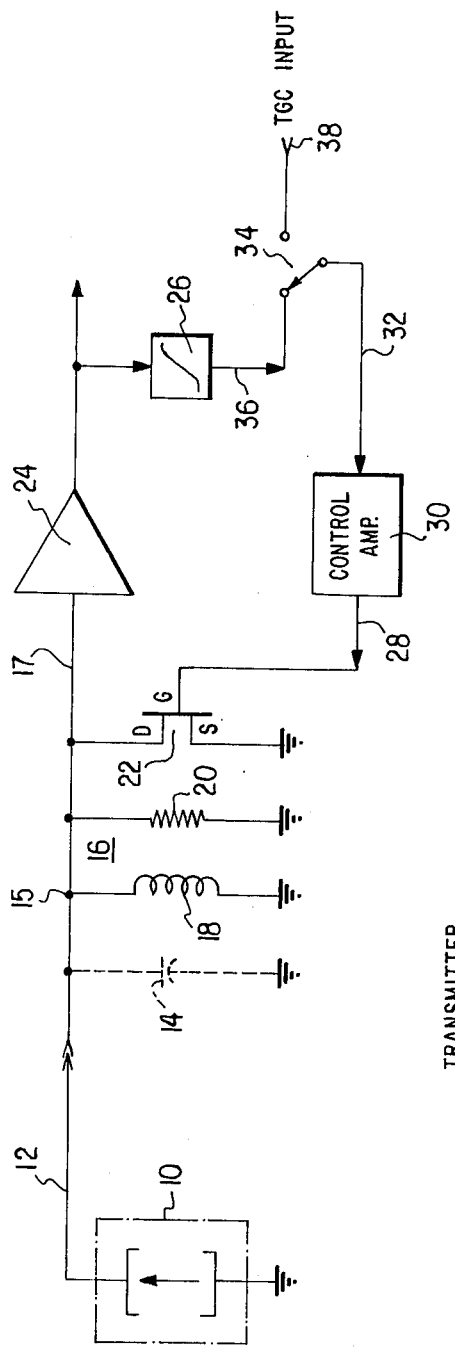
FIG. 1 is a simplified schematic diagram of a circuit in accordance with a preferred embodiment of invention.

With reference now to the drawings, a signal source 10 preferably comprises a piezoelectric transducer of the kind which provides an ultrasonic signal when suitably stimulated. In a practical application of the invention, the transducer may have a capacitive impedance on the order of 200 pf and it may constitute one of a plurality of such transducers in a multi-transducer array. Although the invention is not so limited, the transducer array may be of the kind used for medical diagnosis applications, wherein the ultrasonic energy reflected from the target to the transducers causes the latter to respond by providing a signal.

As shown in the drawings, transducer 10 is coupled to input terminal 15 of a filter 16 by means of a cable 12 which may have a capacitive impedance on the order of 100 pf. The combined capacitive impedance C of transducer 10 and cable 12 is represented in the drawing by an equivalent capacitance 14. The latter is indicated in broken lines in FIG. 1 and it is effectively presented to filter 16, i.e. it is seen by the filter, between input terminal 15 and a voltage reference point such as ground. While the present invention is not so limited, filter 16 is shown as a single pole filter wherein each of the respective filter elements is connected between terminal 15 and ground. An inductive filter element 18, which has an impedance L, is connected between terminal 15 and ground, in parallel with a resistive filter element 20.

In the simplified circuit diagram of FIG. 1, terminal 15 is shown as being directly coupled to the input 17 of a receiver 24, the latter term designating a single amplifier channel in a multi-channel, monolithic receiver unit. Receiver 24 may constitute the initial amplification stage and associated circuitry of a multistage amplifier to which the source signal is applied. Alternatively, a receiver having a single amplification stage may be used. A field effect device 22, e.g. a JFET device, has its drain connected to input 17 of receiver 24 and its source connected to ground. Thus, the impedance of the drain-to-source path, which varies with the voltage on the gate of device 22, is shunted across the input of receiver 24. The output of receiver 24 is connected to an integrating circuit 26, e.g. an envelope detector or the like, which substantially averages the signal derived at the output of receiver 24.

The output of circuit 26 is connected to one of a pair of switch terminals of a switch 34. The other switch terminal is connected to a time gain control input 38 which is explained in greater detail below. The movable arm of switch 34 is connected to the input 32 of a control amplifier 30, whose output 28 is connected to the gate of the aforesaid field effect device 22. Although switch 34 is represented as having a movable mechanical arm capable of selectively switching between the aforesaid switch terminals, it will be understood that the invention is not so limited and that electronic switching means may be employed instead. In still another variation of the invention, a selection of both switch terminals may be made for simultaneous connection to control amplifier input 32.

When device 22 is cut off, the source impedance seen by receiver 24 depends largely on the value R of resistive filter element 20, which is shown as a fixed resistance in FIG. 1. As previously explained, the source impedance must be substantially equal to $R_N$, the internal noise impedance of the receiver, if receiver sensitivity is to be optimized. Further, to obtain the optimum signal-to-noise ratio at the receiver input, it is necessary that filter 16 have a specific bandwidth. Since that bandwidth is determined by the product of R and C, i.e. the impedance values of resistive filter element 20 and equivalent capacitance 14, these two impedances must be matched to each other. With the value of R set substantially at $R_N$, as determined by the above-discussed requirement for maximum receiver sensitivity, the value of C determines the bandwidth of the filter. In the event that the combined capacity of transducer 10 and cable 12 fails to bring equivalent capacitance C to the proper capacitive impedance value, e.g. when R is too large to allow sufficient bandwidth, an additional impedance transformation is required, as discussed in greater detail below. Having thus determined the value of the equivalent capacitance presented to filter 16, the value L of inductive filter element 18 is selected to resonate with C at the operating frequency of the transducer. Thus, the response of the filter is centered on the aforesaid operating frequency.

Field effect device 22 preferably comprises a single JFET device which is selected to have a specified drain-to-source resistance $r_{DSO}$ under zero gate conditions, i.e. when the gate and the source are at the same potential. Specifically, device 22 is selected such that the ratio $R_N/r_{DSO}$ exceeds, or is at least equal to, the additional dynamic range required for receiver 24 to accommodate the dynamic range of the signal on input 17. With the impedance value of device 22 so chosen, the parameters of control amplifier 30 are selected so that the gate of device 22 is properly biased and the control voltage appearing on output 28 can be scaled to drive device 22 to cut-off under specified operating conditions.

In operation, input 32 of control amplifier 30 may be energized either from integrating circuit 26, or from time gain control input 38. Assuming the latter to be the case, the TGC signal applied to control amplifier 30 will vary in accordance with a pre-programmed timing function. Hence, the control signal applied to the gate of field effect device 22 is likewise programmed under these conditions. The desired action is to place a control signal on the gate of field effect device 22 which will vary the impedance of the drain-to-source path in a manner that enables receiver 24 to accept the full dynamic range of the predicted signal applied to input 17. Specifically, since the drain-to-source path is connected in parallel with resistive filter element 20, the variation of the path impedance then controls the peak voltage developed at the input of amplifier 24. For time gain control operation, the pre-programmed signal applied to control amplifier 30 thus must predict the amplitude variation of the source signal.

When switch 34 connects control amplifier 30 to integrating circuit 26, which is itself connected to the output of receiver 24, the impedance of the drain-to-source path of device 22 is varied under adaptive control, i.e. in accordance with the output signal of receiver 24 and hence as a function of the source signal provided by piezoelectric transducer 10. When a strong source signal current is received at receiver input 17, field effect device 22 is biased negatively to increase its conductance and hence the impedance of the drain-to-source path is lowered. Through a suitable choice of the parameters of the circuit components, the source signal appearing at input 17 is thus controlled to remain below the level at which receiver 24 limits.

Since the drain-to-source path is connected in parallel with fixed resistance 20, when the path impedance is lowered, the selectivity of filter 16 decreases and the filter pass band becomes wider. This action also decreases the duration of the filter impulse response, which is defined as the output waveform observed in response to a narrow excitation pulse. This decreased response duration is due to the fact that, as the duration of a pulse decreases, its spectrum increases. Thus, by increasing the filter band width, more frequencies are allowed to pass and hence the duration of the output pulse is shortened.

The decreased duration of the impulse response is a desirable feature of the present invention. It is particularly valuable in medical diagnostic applications, where the signal provided by the transducer represents an echo carrying range information. The narrower the impulse response can be made under these conditions, the more accurately can the source of the echo be localized. The application of a high-amplitude signal to receiver input 17, by lowering drain-to-source impedance, also decreases filter selectivity. This is acceptable from a system point of view because a strong (high-amplitude) signal implies a high signal-to-noise ratio. When such conditions prevail, the need for filtering for the purpose of increasing receiver sensitivity is obviously lessened.

Conversely, when a low amplitude signal is applied to receiver input 17, the drain-to-source impedance of device 22 increases. When the applied signal falls below a predetermined value field effect device 22 cuts off entirely, thereby causing the shunt loading of filter 16 to be that of fixed resistive filter element 20. As previously explained, the value R of resistor element 20 is selected so that the source impedance seen by receiver 24 substantially equals $R_N$. Further, the impedance C of equivalent capacitance 14 is selected relative to R to provide a filter bandwidth which maximizes the signal-to-noise ratio at the receiver input. Hence, when a low amplitude signal is applied to receiver input 17 and device 22 is cut off, optimum signal-to-noise conditions prevail at the input of receiver 24 and the latter operates at maximum sensitivity.

Figure 2:
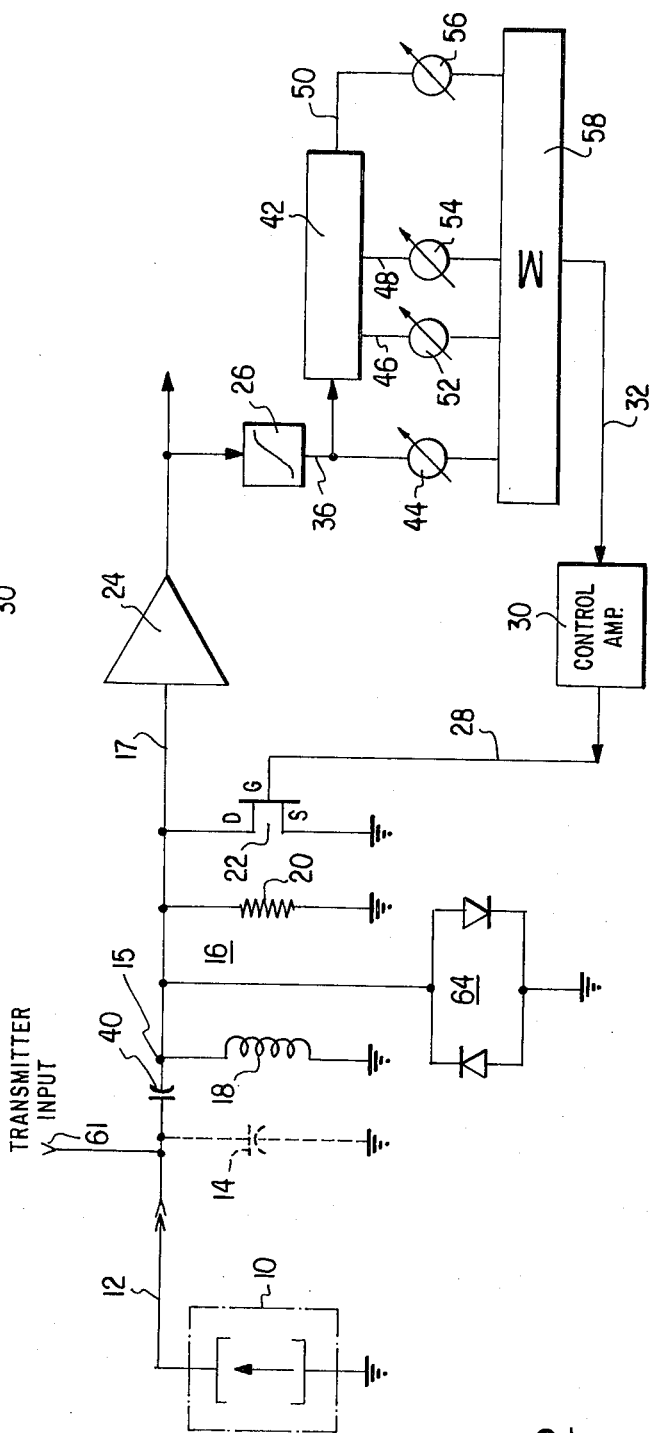
FIG. 2 illustrates a variation of the circuit of FIG. 1.

FIG. 2 illustrates a variation of the circuit of FIG. 1 in which applicable reference numerals have been carried forward. As shown, the source signal from transducer 10 is coupled to filter input terminal 15 by way of cable 12 and a coupling capacitor 40. A transmitter input 61 is provided to couple a high voltage pulse to transducer element 10 in order for the transducer to radiate ultrasound energy, as explained above. A pair of identical diodes 64 is connected in back-to-back arrangement between terminal 15 and ground. Capacitor 40 and diodes 64 protect receiver 24 from the high voltage transmitter pulse. Capacitor 40 also performs a matching function in order to bring the product of the equivalent capacitance C and the source impedance seen by receiver 24 to the requisite value to provide the desired bandwidth. Such matching may be required in the event that the optimum source impedance, whose value is substantially equal to $R_N$, is too large. As in the case of the circuit of FIG. 1, capacitor 14, shown in broken lines, represents the combined capacitance of transducer 10 and cable 12. However, equivalent capacitance C, which resonates with inductance L, here includes the capacitance of coupling capacitor 40.

The circuit shown in FIG. 2 used adaptive control to regulate the drain-to-source impedance of device 22. The output of receiver 24 is connected to integrating circuit 26 which, in the present embodiment, preferably detects the envelope of the received signal to provide a corresponding signal on its output 36. The latter output is connected to a tapped delay line 42 which has a plurality of taps. For the sake of clarity of illustration, only three taps are shown in FIG. 2, designated by the reference numerals 46, 48—50 respectively. Adjusting potentiometers 52, 54—56 are connected between taps 46, 48—50 respectively and a summing circuit 58. Output 36 is further connected to an adjusting potentiometer 44, which in turn is connected to input 32 of control amplifier 30, the output 28 of which is connected to the gate of device 22.

Potentiometers 44, 52, 54—56 are provided to adjust the "weights" of the respective tap signals applied to summing circuit 58. If all tap weights are adjusted to be equal, the output of summing circuit 58 provides a "moving window average" signal to control amplifier 30, adapted to provide a limited amount of memory. It will be clear that other circuitry for averaging the output signal of receiver 24 may be used prior to the application of the signal to control amplifier 30.

Figure 3:
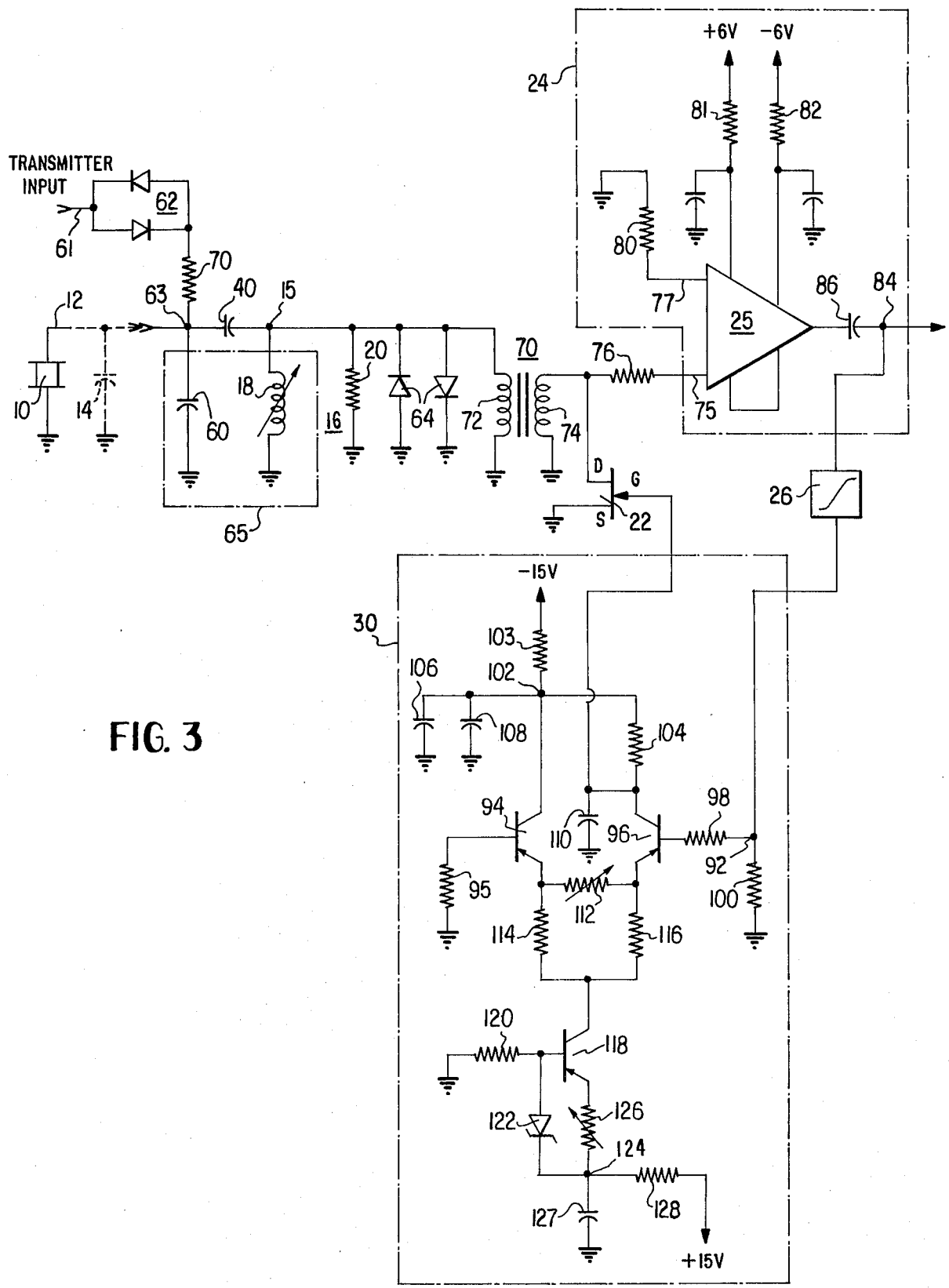
FIG. 3 is a schematic circuit diagram which illustrates an actual embodiment of a circuit in accordance with the principles of the present invention.

The schematic circuit diagram of FIG. 3 illustrates a single channel of an actual embodiment of the present invention in which applicable reference numerals have been retained. With the embodiment under consideration as many as 54 receiver channels may be available for use with an ultrasonic transducer array having a like number of transducers. Consistent with the illustration of a single receiver channel 24, a single piezoelectric transducer 10 is shown which is adapted to provide a source signal at its own ultrasonic frequency for application to receiver 24. As explained above, transducer 10 is capable of radiating energy to a specific target in response to the application thereto of an energizing signal from transmitter 61. Upon detection by transducer 10 of an echo from the target, the source signal is generated.

The transmitter signal is applied to transducer 10 by way of a pair of oppositely poled diodes, collectively designated by the reference numeral 62. The function of these diodes is to provide a voltage sensitive switch which is closed during the time when a high voltage transmitter pulse is supplied to transducer 10 from input 61, and open when input 61 is at zero voltage. A resistor 70 is connected between diodes 62 and a junction point 63 and serves to dampen out any ringing induced by the sudden application of the transmitter pulse.

Upon receipt of the echo that follows the application of ultrasonic energy to the target by transducer 10 in response to a signal from transmitter 61, the transducer generates a source signal. This source signals is coupled to terminal 63 by way of cable 12 and thence to filter input terminal 15 by way of coupling capacitor 40. As before, filter 16 comprises a fixed resistor element 20 and an inductive fiber element 18, the latter being variable in the present embodiment so that tuning to resonance with equivalent capacitance C is readily accomplished.

The circuit shown in FIG. 3 further includes a pad capacitor 60 connected between junction point 63 and ground. Pad capacitor 60 and coupling capacitor 40 combine with capacitance 14, (the latter representing the combined capacitance impedance of transducer 10 and cable 12), to constitute the aforesaid equivalent capacitance C. In the embodiment of the invention illustrated in FIG. 3, capacitor 40 performs the functions of signal coupling, receiver protection and impedance matching. Pad capacitor 60 functions to adjust the shunt capacity presented to the circuit jointly with capacitor 14 to a predetermined value in order to provide the desired bandwidth at the center frequency of transducer 10. Inductive filter element 18 is set to resonate with equivalent capacitance C, seen at terminal 15, at the desired center frequency of the pass band. Practical capacitor values applicable to the circuit of FIG. 3 for different transducer center frequencies and the corresponding inductance values are as follows:

| $f_0$ | $C = (C_{14} + C_{60})$ | L |
| --- | --- | --- |
| 2.25 MHz | 200 pf | 20.0 uh |
| 3.5 MHz | " | 8.6 uh |
| 5.0 MHz | " | 4.2 uh |

Inductance 18 and pad capacitor 60 are shown as being jointly mounted on a pad 65, illustrated in broken line outline in FIG. 3. Alternatively, only one of these components may be pad-mounted. The pad is removable and may be interchanged with other pads carrying the same components, but having different impedance values. Thus, the circuit which constitutes the subject matter of the present invention may be readily adapted for use with transducers operating at different center frequencies, without loss of the cost advantage inherent in the mass production of substantially the same circuit for each channel of the aforesaid multi-channel gain block.

Filter terminal 15 is further coupled to ground by way of a pair of oppositely poled diodes 64, whose function is to provide a path for the charging/discharging currents flowing into/out of capacitor 40 during the sudden application/removal of the high voltage at transmitter input terminal 61. The filter output is further connected to primary winding 72 of a transformer 70, whose secondary winding 74 is coupled to one input 75 of receiver 24 by way of resistor 76. Resistor 76, which may be omitted without substantially changing the operation of the circuit, has a small value and provides damping to prevent the possibility of amplifier oscillation.

As previously explained, receiver 24 may comprise a single amplification stage, such as shown in FIG. 3, or it may constitute a multiple amplification stage receiver. For the purpose of the present explanation, receiver 24 is assumed to contain only a single amplification stage which is represented in FIG. 3 by amplifier 25. In addition to the aforesaid resistor 76, amplifier 25 includes a further input 77, connected to ground by way of a resistor 80. Amplifier 25 also includes a pair of terminals which are coupled to +6 V and −6 V DC supply voltages by way of resistors 81 and 82 respectively. Each of the last-mentioned amplifier terminals is also capacitively coupled to ground. The combination of resistors 81 and 82 respectively and the capacitors that respectively couple the terminals to ground, provide by-pass filtering for the aforesaid supply voltages. A capacitor 86 is connected in series with the output of amplifier 25 and a junction point 84.

In a receiver which has multiple amplification stages, junction point 84 is connected to the subsequent stage, as indicated by the arrow in FIG. 3. For purposes of the present discussion, a single amplification stage is assumed and junction point 84 constitutes the output of receiver 24. This output is connected to integrating circuit 26 and thence to the input of control amplifier 30, designated by a junction point 92. In the illustrated embodiment of the invention, control amplifier 30 is seen to include a pair of transistors 94 and 96 respectively. Junction point 92 is connected to the base of transistor 96 by way of a resistor 98. The base of transistor 96 is also referenced to ground by the presence of a resistor 100, which is connected between junction point 92 and ground. The base of transistor 94 is coupled to ground by means of a resistor 95.

The collector of transistor 94 is coupled to a −15 V DC potential by way of a junction point 102 and a resistor 103. Junction point 102 is coupled to ground through a pair of capacitors 106 and 108. The collector of transistor 96 is likewise coupled to the −15 V DC potential by way of a resistor 104 which is connected to junction point 102. The same collector is capacitively coupled to ground by way of a capacitor 110 and it is further connected to the gate of device 22.

The emitters of transistors 94 and 96 are coupled together by means of a variable resistance 112, e.g. a potentiometer. The latter is connected in parallel with a pair of series-connected resistors 114 and 116. The junction point between the last-recited resistors is connected to the collector of a further transistor 118 whose base is coupled to ground by way of a resistor 120. The emitter of transistor 118 is coupled to a junction point 124 by way of a variable resistor or potentiometer 126 and then to ground through a capacitor 127. Junction point 124 is further coupled to a +15 V DC potential by way of a resistor 128. A Zener diode 122 is connected between the base of transistor 118 and junction point 124 to maintain a constant voltage therebetween.

The particular values chosen for the components of the circuit illustrated in FIG. 3 result, in some instances, from various trade-offs that are made in the design of the overall circuit. It should be noted that the circuit so provided permits a second tranducer signal to be applied to the input terminal of the transformer primary 72, e.g. at junction point 15, so that both transducer signals may be summed for subsequent processing.

At the selected resonant frequency, the values of L and C establish a tuned circuit which has a bandwidth that is largely determined by resistor 20. The latter was selected to have a value of 510 ohms in the illustrated embodiment of the invention. Amplifier 25, which may be, for example, a μA733 differential video amplifier unit commercially available from Fairchild or Motorola, requires a 1000 ohm source impedance for maximum sensitivity. Thus, the function of transformer 70 is to provide a 2:1 step-up of the impedance seen by the amplifier for optimum operation.

It will be noted that the differential amplifier arrangement used in control amplifier 30 has a bias current that can be varied by means of potentiometer 126. This potentiometer, which is connected between the emitter of transistor 118 and terminal 124, allows the zero control voltage, gate bias point of device 22 to be manually adjusted. Thus, the gain of control amplifier 30 is adjustable by means of potentiometer 126. In practice, the bias point is selected to yield a particular output voltage for a predetermined input current. The gain is then adjusted by variable resistor 112 so that the gate of the JFET device is at pinch-off for a particular value of input voltage. Alternatively, variable resistance 112 may be dispensed with in favor of a fixed gain amplifier and a scaling arrangement.

As previously explained, the embodiment of the invention shown in FIG. 3 illustrates a circuit for a single receiver channel of a 54-channel monolithic amplifier unit which enables the reciever channel to operate with a corresponding transducer of an ultrasonic transducer array that has a like number of individual transducers. By using multiple amplification stages in each channel, a 40 dB fixed gain mode of operation is possible in each channel, with a dynamic range calculated to be on the order of 60 dB. By using the circuit which forms the subject matter of the present invention in each channel, source signals having a dynamic range of up to 90 dB can be readily accepted by the respective receiver channels.

As already mentioned, various trade-offs are possible. For example, if receiver performance at less than optimum sensitivity is acceptable, matching to achieve the optimum signal-to-noise ratio at the receiver input may not be required. Capacitor matching may be carried out through pad capacitor 60 and coupling capacitor 40. While capacitor 60 and inductive filter element 18 may be jointly positioned on removable pad 65, the invention is not so limited and either component alone may be mounted on the pad. In either case, the removability of the pad permits it to be exchanged for other pads carrying components that have different values. In this manner, the same basic receiver circuit may be used in each channel, matched to the different center frequencies of the respective transducers of the array.

The averaging circuit shown in FIG. 2 may be replaced by other, more sophisticated circuits, e.g. by a circuit which generates an estimate of the output signal level and which uses the difference between the actual signal and the estimate as a means of developing the input drive for the control amplifier. Also, for certain situations a simple RC filter may be adequate. In either case, the purpose is to accomplish averaging of the signal received at the output of receiver 24 and to bias the gate of device 22 accordingly.

As previously explained, receiver 24 may include multiple stages of amplification. For example, amplifier 25 may be used as a differential output amplifier connected to the input terminal pair of a second differential amplification stage substantially identical to amplifier 25. Subsequent amplification stages may be similarly connected to the immediately preceding stage. In the latter instance, the control amplifier may constitute a transistor quad of the type that is available from Texas Instrument Company under the designation Q2T2905, wherein both halves are connected substantially in the manner shown in FIG. 3 for one pair of transistors. Additional JFET devices may then be connected, with one device connected across the dual inputs of each amplification stage following the first stage. The gate of each such additional JFET device may then be energized from the second half of the control amplifier, substantially in the same manner in which the gate of device 22 is energized from the first half.

While the circuit which comprises the subject matter of the present invention lends itself to either adaptive or deterministic (TGC) control of the drain-to-source impedance of device 22, these two types of control are not incompatible with each other and under certain conditions it may be desirable to combine them. For example, the output of integrating circuit 26 could be subtracted from a deterministic control signal to form the input of the control amplifier. Such a connection may allow for a reduction in the complexity of the adaptive control process by using the deterministic portion of the control to compensate for average variations of signal levels that are known a priori. Further, the adaptive feature then allows for deviations from the average to be corrected.

It will be apparent from the foregoing discussion that the present invention lends itself to numerous variations, modifications, substitutions and equivalents which will now occur to those skilled in the art and which fall within the spirit and scope contemplated by the invention. Accordingly, it is intended that the invention be limited only by the scope of the claims appended hereto.

What is claimed is:

1. A circuit for variably adapting the dynamic range of an electrical signal to the predetermined dynamic range of a signal receiver, said signal being derived from an ultrasonic signal source for application to the input of said receiver;

said circuit comprising:
   a filter coupled to said receiver input, said filter including at least resistive and inductive filter elements adapted to provide a frequency pass band centered substantially on a predetermined operating frequency of the source signal;
   means for coupling said source signal to said filter;
   an equivalent capacitance presented to said filter substantially in parallel with the latter, said equivalent capacitance including at least the combined capacitance of said source and said coupling means;
   said inductive filter element being selected to resonate with said equivalent capacitance substantially at said predetermined operating frequency;
   field effect device means including gate means and a drain-to-source path, said drain-to-source path being connected substantially in shunt with said receiver input; and
   means for applying a control signal to said gate means adapted to vary the resistance of said drain-to-source path;
   whereby said control signal is adapted to limit the amplitude of the signal applied to said receiver input substantially to the dynamic range of said receiver.

2. A circuit in accordance with claim 1, wherein the impedance of said resistive filter element is selected to substantially equal the receiver noise impedance reflected to said receiver input;
   whereby the sensitivity of said receiver is maximized.

3. A circuit in accordance with claim 2 wherein the impedance values of said resistive filter element and of said equivalent capacitance are matched to each other to provide the filter bandwidth required for optimum signal-to-noise conditions at said receiver input.

4. A circuit in accordance with claim 3 wherein said coupling means includes a cable for coupling said signal from said source to said filter, the capacitance of said cable forming a part of said equivalent capacitance; and
   wherein said equivalent capacitance further includes additional capacitive means selected so that the product of the impedance of said equivalent capacitance and said source impedance substantially determines the required bandwidth for said optimum signal-to-noise conditions.

5. A circuit in accordance with claim 4 wherein said filter includes a common junction point;
   said resistive filter element comprising a fixed resistor connected between said junction point and a voltage reference point; and
   said inductive filter element comprising a variable inductance connected in parallel with said fixed resistor.

6. A circuit in accordance with claim 5 wherein said additional capacitive means comprises at least a coupling capacitor connected between said cable and said junction point.

7. A circuit in accordance with claim 5 wherein said additional capacitive means comprises at least a pad capacitor connected between said cable and said reference point.

8. A circuit in accordance with claim 7 and further including a removable pad having at least said variable inductance mounted thereon;
   whereby said receiver may be matched to different signal sources by selectively exchanging said pad for others which have component impedance values appropriately scaled to the respective operating frequencies of said different signal sources.

9. A circuit in accordance with claim 8 wherein said removable pad further carries said pad capacitor.

10. A circuit in accordance with claim 7 and further comprising a transformer including primary and secondary windings:
   said primary winding being coupled between said common junction point of said filter and said reference point; and
   said secondary winding being coupled substantially between said receiver input and said reference point in parallel with said field effect device means.

11. A circuit in accordance with claims 2 or 3 wherein said receiver noise impedance has a value $R_N$; and
   wherein said field effect device means comprises a single JFET device including a source element, a drain and a gate, said device having a predetermined drain-to-source resistance $r_{DSO}$ when said gate and said source element are at the same potential, said JFET device being selected to provide a ratio $R_N/r_{DSO}$ at least equal to the difference between the dynamic range of said source signal and said receiver.

12. A circuit in accordance with claim 2 or 10 wherein said receiver noise impedance has a value $R_N$;
   said field effect device means comprising a single JFET device including a source element, a drain and a gate, said device having a predetermined drain-to-source resistance $r_{DSO}$ when said gate and said source element are at the same potential, said JFET device being selected to provide a ratio $R_N/r_{DSO}$ at least equal to the difference between the dynamic range of said source signal and said receiver;
   said means for applying said control signal comprising a control amplifier having its output coupled to said gate; and
   means adapted to be connected to the input of said control amplifier for varying said control signal;
   whereby said control signal is adapted to decrease the drain-to-source resistance of said device when the amplitude of the signal applied to said receiver input exceeds a predetermined limit.

13. A circuit in accordance with claim 12 wherein said means for varying said control signal comprises time gain control means for providing a predetermined timing function, said timing function being adapted to change the voltage applied to said gate when said predetermined signal limit is exceeded.

14. A circuit in accordance with claim 13 wherein said means for varying said control signal further includes adaptive control means responsive to the amplitude of the signal derived from said receiver to change the voltage applied to said gate when said predetermined signal limit is exceeded.

15. A circuit in accordance with claim 12 wherein said means for varying said control signal comprises adaptive control means, said adaptive control means including signal integrating means connected between said receiver and said control amplifier input adapted to average the signal derived from said receiver for application to said control amplifier.

16. A circuit in accordance with claim 15 wherein said receiver includes at least a first amplification stage; and
   wherein said signal integrating means is connected to provide a signal to said control amplifier substantially representative of the envelope of the signal derived from said first amplification stage.

17. A circuit in accordance with claim 16 wherein said adaptive control means further comprises a delay line connected to the output of said signal integrating circuit and including a plurality of delay line taps;
   means for varying the tap output signals to provide respective signals of substantially equal weight;
   means for summing the weighted tap signals; and
   means for connecting the output of said summing means to said control amplifier input adapted to apply a moving window average signal thereto.

18. A circuit in accordance with claims 1 or 10 wherein said signal source constitutes one of a plurality of ultrasonic transducers of a transducer array each adapted to provide a separate one of said electrical signal;
   said receiver substantially forming a single channel of a monolithic, multi-channel amplifier unit wherein each channel corresponds to one of said transducers; and
   said circuit constituting one of a plurality of substantially similar circuits each connected to one of said receivers and adapted to match the latter to the operating frequency of its corresponding transducer.

* * * * *